US006811982B2

(12) United States Patent
Gonzalgo et al.

(10) Patent No.: US 6,811,982 B2
(45) Date of Patent: Nov. 2, 2004

(54) CANCER DIAGNOSTIC METHOD BASED UPON DNA METHYLATION DIFFERENCES

(75) Inventors: Mark L. Gonzalgo, Baltimore, MD (US); Peter A. Jones, La Canada, CA (US); Gangning Liang, Rowland Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 10/109,725

(22) Filed: Mar. 28, 2002

(65) Prior Publication Data

US 2002/0177154 A1 Nov. 28, 2002

Related U.S. Application Data

(63) Continuation of application No. 09/887,941, filed on Jun. 22, 2001, which is a continuation of application No. 09/094,207, filed on Jun. 9, 1998, now Pat. No. 6,251,594.
(60) Provisional application No. 60/049,231, filed on Jun. 9, 1997.

(51) Int. Cl.[7] ........................... C12Q 1/68; C12P 19/34; C07H 21/02; C07H 21/04
(52) U.S. Cl. ..................... 435/6; 435/91.2; 435/91.21; 536/24.31; 536/24.33; 536/23.5
(58) Field of Search ....................... 435/6, 91.2, 91.21; 536/24.31, 24.32, 24.33, 23.5

(56) References Cited

U.S. PATENT DOCUMENTS

| 5,756,668 A | * | 5/1998 | Baylin et al. ................ 530/350 |
| 5,786,146 A | | 7/1998 | Herman et al. |
| 6,017,704 A | | 1/2000 | Herman et al. |
| 6,251,594 B1 | * | 6/2001 | Gonzalgo et al. .............. 435/6 |

OTHER PUBLICATIONS

Gonzalgo et al., Rapid quantitation of methylation differences at specific sites using methylation–sensitive single nucleotide primer extension (MsSNuPE). *Nucleic Acids Research* 25(12):2529–2531, 1997.

Herman et al., Methylation–specific PCR: A novel PCR assay for methylation status of CpG islands. *Proc. Natl. Acad. Sci.* 93:9821–9826, 1996.

Zhou et al., Use of a single sequencing termination reaction to distinguish between cytosine and 5–methylcotosine in bisulfite–modified DNA. *BioTechniques* 22(5):850–853, 1997.

* cited by examiner

*Primary Examiner*—Carla J. Myers
(74) *Attorney, Agent, or Firm*—Barry L. Davison; Davis Wright Tremaine LLP

(57) ABSTRACT

There is disclosed a cancer diagnostic method based upon DNA methylation differences at specific CpG sites. Specifically, the inventive method provides for a bisulfite treatment of DNA, followed by methylation-sensitive single nucleotide primer extension (Ms-SNuPE), for determination of strand-specific methylation status at cytosine residues.

10 Claims, 5 Drawing Sheets

SEQUENCE LISTING

<160> NUMBER OF SEQ ID NOS: 17

<210> SEQ ID NO 1
<211> LENGTH: 530
<212> TYPE: DNA
<213> ORGANISM: homo sapiens

<400> SEQUENCE: 1

```
cccgcgacct aagccagcga cttaccacgt tagtcagcta agaagtggca gagctgggat      60
tcgaacctat aaagaactct gaagcctggg tattttttaca tgacacttta cataatgcgc    120
cacggggtag tcggaggggg aggtccatct ccctttccct tgctgtccat ctccacagaa    180
aagaagcaag tggaggacag gagccagaaa gtcatctggc cgcggatcat tccggagtga    240
cccccgccgc caccactcgc atagtccgct tatggcggga gggcacctca gagattctca    300
caggggctgt gcggccagaa ccagaagtgc aaagcaccgt tagcgactct atcgccccct    360
gccgcctgtg gcgcccagtc cgaagctgct gttttcagga gggctagtgg gctaagaaaa    420
gagctcaccg actgactgcc caacagctgt tgcgagccag tgctaggctg cagacagcct    480
tgccaaatgt ggtgacataa gcgggagggg ggaacattta gagagcccta                530
```

<210> SEQ ID NO 2
<211> LENGTH: 308
<212> TYPE: DNA
<213> ORGANISM: homo sapiens

```
<400> SEQUENCE: 2
ctagggtagg ctggtctgtg ctggatacgc gtgttcttct gcggagttaa agggtcgggg      60 acggggttc  tggacttacc agagcaattc cagccggtgg gcgtttgaca gccacttaag     120
gaggtaggga aagcgagctt caccgggcgg gctacgatga gtagcatgac gggcagcagc     180
agcagcagcc agcaaaagcc tagcaaagtg tccagctgct gcactgccgc ggggactccc     240
acatcaccat gactagttgt gcaactctgc agcagaaacg gcttccgagg aacacaggat     300
cgcgggggg                                                             308

<210> SEQ ID NO 3
<211> LENGTH: 177
<212> TYPE: DNA
<213> ORGANISM: homo sapiens

<400> SEQUENCE: 3
gcttcctttt tctcggcttt cctcactatc ctctccctgt tcgagagtat ctccaccagc      60
accgagcctc acacgggctg tgcctccatc tttggaatgc ctaccttcct ttcttgcgaa     120
gcccctccca gggccagccc ttgtgcaccg gctcaagggg actgctctcc tgcctcg       177

<210> SEQ ID NO 4
<211> LENGTH: 148
<212> TYPE: DNA
<213> ORGANISM: homo sapiens

<400> SEQUENCE: 4
ttgcgccgat cgtcaagaac ctctcatccc tggcagcagc aaagccaata tatttccatt      60
tcttatttca gtttgccacc aaaacaaagc tgcgcgcggc tgagggcagg aaggcgctga     120
gaccgaccga gaagaaggga cgtcccgg                                        148

<210> SEQ ID NO 5
<211> LENGTH: 384
<212> TYPE: DNA
<213> ORGANISM: homo sapiens

<400> SEQUENCE: 5
caggcccgcc gagactccac tccaactacc aggaaatttc ccgtggagct tcaattcctg      60
ggaccctcct actgcgggga gagtggtttc cctgccccac accatgccct aggcccgagt     120
ctgcggctct tggggatct  ctccgagctc cgacaccgtg ttcggaccgg gtgcgccctg     180
ccgctggggc tcaagcctgc aggcgtgaga accgggggac tctctatggc accaagagct     240
tcaccgtgag cgtaggcaga agcttcgctt tgatcctagg gcttacaaag tcctcctttg     300
gctgcccatg atggtaaaag ggcagttgct cacaaagcgc gagtgtgtgt gccagacagt     360
gtaaatgagt gttgggaccg gcgt                                            384

<210> SEQ ID NO 6
<211> LENGTH: 178
<212> TYPE: DNA
<213> ORGANISM: homo sapiens

<400> SEQUENCE: 6
gggtccgttc gtgaatgcat gagcagggtg tgagcgccag ggggttacac ttctcacggg      60
ttaaacccca gacaacttca cgagggaacc acgtgccatt ttaacagcgt acggtcggga     120
tcgtgggacg tcattaaacg gagtgggttg agtatgtgac tctgtcaccc attttctg       178
```

```
<210> SEQ ID NO 7
<211> LENGTH: 359
<212> TYPE: DNA
<213> ORGANISM: homo sapiens

<400> SEQUENCE: 7
ccccgcgggg cagaatccaa gtgagtcaga cacattgctc cctccctgct gctgccagtc    60
catctctttg ccaacaaacc tgcttaaaat gccaaagctg gtccaaagtt tcaggaaaac   120
aacttccgcc agagggcacg tagagggcac agatgctata gatgcttctc tgacaaacac   180
tcctgacccc cttgacagat tggaaaatac atggttcaga aagggtgaga gatttcaact   240
tgagaagtga aactaggaaa agatggaagg tgtccggatt tctagctcaa gtccacacac   300
tgcttctgct gcggtgacta aatcgtggct gtgttctcat cacctgcctc gcggcgcgc    359

<210> SEQ ID NO 8
<211> LENGTH: 251
<212> TYPE: DNA
<213> ORGANISM: homo sapiens

<400> SEQUENCE: 8
ggcgggcctg ggcaccgcgg agggggggct tttctgcgcc cggcgaagcg tggaacttgc    60
gccctgaggc agcgcggcga gaccagtcca gagaccgggg cgagcctcct caggattcct   120
cgccccagtg cagatgctgt gagcttagac gaggacaggg catggcactc ggcttggccc   180
gtagtggacg tgttttttgc agtcatgaac ccaaacgccg caaaccttga ccgtttcccc   240
acccgtgttg t                                                        251

<210> SEQ ID NO 9
<211> LENGTH: 145
<212> TYPE: DNA
<213> ORGANISM: homo sapiens
<220> FEATURE:
<221> NAME/KEY: misc_feature
<222> LOCATION: (126)..(126)
<223> OTHER INFORMATION: undetermined base residue
<220> FEATURE:
<221> NAME/KEY: misc_feature
<222> LOCATION: (127)..(127)
<223> OTHER INFORMATION: undetermined base residue

<400> SEQUENCE: 9
tgagagcagc atcctcccct gcgtgtggtt ctctaactta cctcctgtat ggggtctgcg    60
gacccagcac acctcccggg ccccaaaaa attccagctc aagagcccta aaaatccta    120 ccctgnnaaa gtttgagctt ctccc                                        145

<210> SEQ ID NO 10
<211> LENGTH: 215
<212> TYPE: DNA
<213> ORGANISM: homo sapiens

<400> SEQUENCE: 10
acgccggcca cagttcttca gtgaaacgct tcactctctg gtcatagagg taggaaacta    60
tagctgtccc aactaaatgt caggacgaat tagcccagct ggtcacgctc acagtcaccg   120
cctccaccag actgagcgac cctcccaacg gggtttgccg tgttggagg acagcggagt    180 ttcgttgctg tgtcaatttg tgtagacgcg gctgc                             215
```

```
<210> SEQ ID NO 11
<211> LENGTH: 220
<212> TYPE: DNA
<213> ORGANISM: homo sapiens

<400> SEQUENCE: 11
ctgctctctt tcttcttttt cccctttcct ctcctctccc tttcctcagg tcacagcgga      60
gtgaatcagc tcggtggtgt ctttgtcaac gggcggccac tgccggactc cacccggcag    120
aagattgtag agctagctca cagcggggcc cggccgtgcg acatttcccg aattctgcag    180
gtgatcctcc cggcgccgcc ccactcgccg ccccgcggc                           220

<210> SEQ ID NO 12
<211> LENGTH: 196
<212> TYPE: DNA
<213> ORGANISM: homo sapiens

<400> SEQUENCE: 12
gggcggcacg gagggagtca ggagtgagcc cgaagatgga gagaagtcga ttcgcccaga     60
gaacgcaaga cggtggatca gagatgagtc ccaggaacct cagagagcga ggctgacagg    120
cccggggaga ggaccgggca gggacaaacc agcggacaga gcagagcgcg aaatggttga    180
gaccgggaag cgacct                                                   196

<210> SEQ ID NO 13
<211> LENGTH: 22
<212> TYPE: DNA
<213> ORGANISM: Artificial Sequence
<220> FEATURE:
<223> OTHER INFORMATION: p16 promoter region-specific Ms-SNuPE primer

<400> SEQUENCE: 13
gtaggtgggg aggagtttag tt                                             22

<210> SEQ ID NO 14
<211> LENGTH: 23
<212> TYPE: DNA
<213> ORGANISM: Artificial Sequence
<220> FEATURE:
<223> OTHER INFORMATION: p16 promoter region-specific Ms-SNuPE primer

<400> SEQUENCE: 14
tctaataacc aaccaacccc tcc                                            23

<210> SEQ ID NO 15
<211> LENGTH: 21
<212> TYPE: DNA
<213> ORGANISM: Artificial Sequence
<220> FEATURE:
<223> OTHER INFORMATION: p16 promoter region-specific Ms-SNuPE primer

<400> SEQUENCE: 15 ttttttttgtt tggaaagata t                                             21

<210> SEQ ID NO 16
<211> LENGTH: 18
<212> TYPE: DNA
<213> ORGANISM: Artificial Sequence
<220> FEATURE:
<223> OTHER INFORMATION: p16 promoter region-specific Ms-SNuPE primer
```

```
-continued

<400> SEQUENCE: 16
ttttaggggt gttatatt                                                        18

<210> SEQ ID NO 17
<211> LENGTH: 15
<212> TYPE: DNA
<213> ORGANISM: Artificial Sequence
<220> FEATURE:
<223> OTHER INFORMATION: p16 promoter region-specific Ms-SNuPE primer

<400> SEQUENCE: 17
tttgagggat agggt                                                           15
```

CANCER DIAGNOSTIC METHOD BASED UPON DNA METHYLATION DIFFERENCES

This patent application is a continuation of pending U.S. patent application Ser. No. 09/887,941 filed 22 Jun. 2001, which is a continuation of U.S. patent application Ser. No. 09/094,207, filed 09 Jun. 1998, now U.S. Pat. No. 6,251,594, which claims priority from U.S. Provisional Patent Application 60/049,231 filed 09 Jun. 1997.

TECHNICAL FIELD OF THE INVENTION

The present invention provides a cancer diagnostic method based upon DNA methylation differences at specific CpG sites. Specifically, the inventive method provides for a bisulfite treatment of DNA, followed by methylation-sensitive single nucleotide primer extension (Ms-SNuPE), for determination of strand-specific methylation status at cytosine residues.

BACKGROUND OF THE INVENTION

Cancer treatments, in general, have a higher rate of success if the cancer is diagnosed early and treatment is started earlier in the disease process. The relationship between improved prognosis and stage of disease at diagnosis hold across all forms of cancer for the most part. Therefore, there is an important need to develop early assays of general tumorigenesis through marker assays that measure general tumorigenesis without regard to the tissue source or cell type that is the source of a primary tumor. Moreover, there is a need to address distinct genetic alteration patterns that can serve as a platform associated with general tumorigenesis for early detection and prognostic monitoring of many forms of cancer.

Importance of DNA Methylation

DNA methylation is a mechanism for changing the base sequence of DNA without altering its coding function. DNA methylation is a heritable, reversible and epigenetic change. Yet, DNA methylation has the potential to alter gene expression, which has profound developmental and genetic consequences. The methylation reaction involves flipping a target cytosine out of an intact double helix to allow the transfer of a methyl group from S-adenosylmethionine in a cleft of the enzyme DNA (cystosine-5)-methyltransferase (Klimasauskas et al., *Cell* 76:357–369, 1994) to form 5-methylcytosine (5-mCyt). This enzymatic conversion is the only epigenetic modification of DNA known to exist in vertebrates and is essential for normal embryonic development (Bird, *Cell* 70:5–8, 1992; Laird and Jaenisch, *Human Mol. Genet.* 3:1487–1495, 1994; and Bestor and Jaenisch, *Cell* 69:915–926, 1992). The presence of 5-mCyt at CpG dinucleotides has resulted in a 5-fold depletion of this sequence in the genome during vertebrate evolution, presumably due to spontaneous deamination of 5-mCyt to T (Schoreret et al., *Proc. Natl. Acad. Sci. USA* 89:957–961, 1992). Those areas of the genome that do not show such suppression are referred to as "CpG islands" (Bird, *Nature* 321:209–213, 1986; and Gardiner-Garden et al., *J. Mol. Biol.* 196:261–282, 1987). These CpG island regions comprise about 1% of vertebrate genomes and also account for about 15% of the total number of CpG dinucleotides (Bird, Infra.). CpG islands are typically between 0.2 to about 1 kb in length and are located upstream of many housekeeping and tissue-specific genes, but may also extend into gene coding regions. Therefore, it is the methylation of cytosine residues within CpG islands in somatic tissues, which is believed to affect gene function by altering transcription (Cedar, *Cell* 53:3–4, 1988).

Methylation of cytosine residues contained within CpG islands of certain genes has been inversely correlated with gene activity. This could lead to decreased gene expression by a variety of mechanisms including, for example, disruption of local chromatin structure, inhibition of transcription factor-DNA binding, or by recruitment of proteins which interact specifically with methylated sequences indirectly preventing transcription factor binding. In other words, there are several theories as to how methylation affects mRNA transcription and gene expression, but the exact mechanism of action is not well understood. Some studies have demonstrated an inverse correlation between methylation of CpG islands and gene expression, however, most CpG islands on autosomal genes remain unmethylated in the germline and methylation of these islands is usually independent of gene expression. Tissue-specific genes are usually unmethylated and the receptive target organs but are methylated in the germline and in non-expressing adult tissues. CpG islands of constitutively-expressed housekeeping genes are normally unmethylated in the germline and in somatic tissues.

Abnormal methylation of CpG islands associated with tumor suppressor genes may also cause decreased gene expression. Increased methylation of such regions may lead to progressive reduction of normal gene expression resulting in the selection of a population of cells having a selective growth advantage (i.e., a malignancy).

It is considered that altered DNA methylation patterns, particularly methylation of cytosine residues, cause genome instability and are mutagenic. This, presumably, has led to an 80% suppression of a CpG methyl acceptor site in eukaryotic organisms, which methylate their genomes. Cytosine methylation further contributes to generation of polymorphism and germ-line mutations and to transition mutations that inactivate tumor-suppressor genes (Jones, *Cancer Res.* 56:2463–2467, 1996). Methylation is also required for embryonic development of mammals (Bestor and Jaenisch, *Cell* 69:915–926, 1992). It appears that that the methylation of CpG-rich promoter regions may be blocking transcriptional activity. Therefore, there is a probability that alterations of methylation are an important epigenetic criteria and can play a role in carcinogenesis in general due to its function of regulating gene expression. Ushijima et al. (*Proc. Natl. Acad. Sci. USA* 94:2284–2289, 1997) characterized and cloned DNA fragments that show methylation changes during murine hepatocarcinogenesis. Data from a group of studies of altered methylation sites in cancer cells show that it is not simply the overall levels of DNA methylation that are altered in cancer, but changes in the distribution of methyl groups.

These studies suggest that methylation, at CpG-rich sequences known as CpG islands, provide an alternative pathway for the inactivation of tumor suppressors, despite the fact that the supporting studies have analyzed only a few restriction enzyme sites without much knowledge as to their relevance to gene control. These reports suggest that methylation of CpG oligonucleotides in the promoters of tumor suppressor genes can lead to their inactivation. Other studies provide data that suggest that alterations in the normal methylation process are associated with genomic instability (Lengauer et al. *Proc. Natl. Acad. Sci. USA* 94:2545–2550, 1997). Such abnormal epigenetic changes may be found in many types of cancer and can, therefore, serve as potential markets for oncogenic transformation, provided that there is a reliable means for rapidly determining such epigenetic changes. The present invention was made to provide such a universal means for determining abnormal epigenetic changes and address this need in the art.

Methods to Determine DNA Methylation

There is a variety of genome scanning methods that have been used to identify altered methylation sites in cancer cells. For example, one method involves restriction landmark genomic scanning (Kawai et al., *Mol. Cell. Biol.* 14:7421–7427, 1994), and another example involves methylation-sensitive arbitrarily primed PCR (Gonzalgo et al., *Cancer Res.* 57:594–599, 1997). Changes in methylation patterns at specific CpG sites have been monitored by digestion of genomic DNA with methylation-sensitive restriction enzymes followed by Southern analysis of the regions of interest (digestion-Southern method). The digestion-Southern method is a straightforward method but it has inherent disadvantages in that it requires a large amount of DNA (at least or greater than 5 μg) and has a limited scope for analysis of CpG sites (as determined by the presence of recognition sites for methylation-sensitive restriction enzymes). Another method for analyzing changes in methylation patterns involves a PCR-based process that involves digestion of genomic DNA with methylation-sensitive restriction enzymes prior to PCR amplification (Singer-Sam et al., *Nucl. Acids Res.* 18:687,1990). However, this method has not been shown effective because of a high degree of false positive signals (methylation present) due to inefficient enzyme digestion of overamplification in a subsequent PCR reaction.

Genomic sequencing has been simplified for analysis of DNA methylation patterns and 5-methylcytosine distribution by using bisulfite treatment (Frommer et al., *Proc. Natl. Acad. Sci. USA* 89:1827–1831, 1992). Bisulfite treatment of DNA distinguishes methylated from unmethylated cytosines, but original bisulfite genomic sequencing requires large-scale sequencing of multiple plasmid clones to determine overall methylation patterns, which prevents this technique from being commercially useful for determining methylation patterns in any type of a routine diagnostic assay.

In addition, other techniques have been reported which utilize bisulfite treatment of DNA as a starting point for methylation analysis. These include methylation-specific PCR (MSP) (Herman et al. *Proc. Natl. Acad Sci. USA* 93:9821–9826, 1992); and restriction enzyme digestion of PCR products amplified from bisulfite-converted DNA (Sadri and Hornsby, *Nucl. Acids Res.* 24:5058–5059, 1996; and Xiong and Laird, *Nucl. Acids Res.* 25:2532–2534, 1997).

PCR techniques have been developed for detection of gene mutations (Kuppuswamy et al., *Proc. Natl. Acad. Sci. USA* 88:1143–1147, 1991) and quantitation of allelic-specific expression (Szabo and Mann, *Genes Dev.* 9:3097–3108, 1995; and Singer-Sam et al., *PCR Methods Appl.* 1:160–163, 1992). Such techniques use internal primers, which anneal to a PCR-generated template and terminate immediately 5' of the single nucleotide to be assayed. However an allelic-specific expression technique has not been tried within the context of assaying for DNA methylation patterns.

Therefore, there is a need in the art to develop improved diagnostic assays for early detection of cancer using reliable and reproducible methods for determining DNA methylation patterns that can be performed using familiar procedures suitable for widespread use. This invention was made to address the foregoing need.

SUMMARY OF THE INVENTION

The present invention provides a method for determining DNA methylation patterns at cytosine sites, comprising the steps of:

(a) obtaining genomic DNA from a DNA sample to be assayed;

(b) reacting the genomic DNA with sodium bisulfite to convert unmethylated cytosine residues to uracil residues while leaving any 5-methylcytosine residues unchanged to provide primers specific for the bisulfite-converted genomic sample for top strand or bottom strand methylation analysis;

(c) performing a PCR amplification procedure using the top strand or bottom strand specific primers;

(d) isolating the PCR amplification products;

(e) performing a primer extension reaction using Ms-SNuPE primers, [$^{32}$P]dNTPs and Taq polymerase, wherein the Ms-SNuPE primers comprise from about a 15 mer to about a 22 mer length primer that terminates immediately 5' of a single nucleotide to be assayed; and (f) determining the relative amount of methylation at CpG sites by measuring the incorporation of different $^{32}$P-labeled dNTPs.

Preferably, the [$^{32}$P]NTP for top strand analysis is [$^{32}$P]dCTP or [$^{32}$P]TTP. Preferably, the [$^{32}$P]NTP for bottom strand analysis is [$^{32}$P]dATP or [$^{32}$P]dGTP. Preferably, the isolation step of the PCR products uses an electrophoresis technique. Most preferably, the electrophoresis technique uses an agarose gel. Preferably, the Ms-SNuPE primer sequence comprises a sequence of at least fifteen but no more than twenty five, bases having a sequence selected from the group consisting of GaL1 (SEQ ID NO:1), GaL2 (SEQ ID NO:2), GaL4 (SEQ ID NO:3), HuN1 (SEQ ID NO:4), HuN2 (SEQ ID NO:5), HuN3 (SEQ ID NO:6), HuN4 (SEQ ID NQ:7), HuN5 (SEQ ID NO:8), HuN6 (SEQ ID NO:9), CaS1 (SEQ ID NO:10), CaS2 (SEQ ID NO:11), CaS4 (SEQ ID NO:12), and combinations thereof.

The present invention further provides a Ms-SNuPE primer sequence designed to anneal to and terminate immediately 5' of a desired cytasine codon in the CpG target site and that is located 5' upstream from a CpG island and are frequently hypermethylated in promoter regions of somatic genes in malignant tissue. Preferably, the Ms-SNuPE primer sequence comprises a sequence of at least fifteen bases having a sequence selected from the group consisting of GaL1 (SEQ ID NO:1), GaL2 (SEQ ID NO:2), GaL4 (SEQ ID NO:3), HuN1 (SEQ ID NO:4), HuN2 (SEQ ID NO:5), HuN3 (SEQ ID NO:6), HuN4 (SEQ ID NO:7), HuN5 (SEQ ID NO:8), HuN6 (SEQ ID NO:9), CaS1 (SEQ ID NO:10), CaS2 (SEQ ID NO:11), CaS4 (SEQ ID NO:12), and combinations thereof. The present invention further provides a method for obtaining a Ms-SNuPE primer sequence, comprising finding a hypermethylated CpG island in a somatic gene am a malignant tissue or cell culture, determining the sequence located immediately 5' upstream from the hypermethylated CpG island, and isolating a 15 to 25 mer sequence 5' upstream from the hypermethylated CpG island for use as a Ms-SNuPE primer. The present invention further provides a Ms-SNuPE primer comprising a 15 to 25 mer oligonucleotide sequence obtained by the process comprising, finding a hypermethylated CpG island in a somatic gene from a malignant tissue or cell culture, determining the sequence located immediately 5' upstream from the hypermethylated CpG island, and isolating a 15 to 25 mer sequence 5' upstream from the hypermethylated CpG island for use as a Ms-SNuPE primer.

BRIEF DESCRIPTION OF THE DRAWINGS

FIG. 3 shows data from an 18 mer oligonucleotide [SEQ ID NO. 16] which was used in multiplex analysis of CpG methylation (site 2) of the p16 5' CpG in combination with a 15-mer and 21-mer primer [SEQ ID NOS 17 and 15, respectively] (correlation coefficient= 0.99). Both the 15 mer and 21-mer produced a nearly identical linear response as the 18-mer. FIG. 3 shows data from three separate experiments.

DETAILED DESCRIPTION OF THE INVENTION

Figure 1:
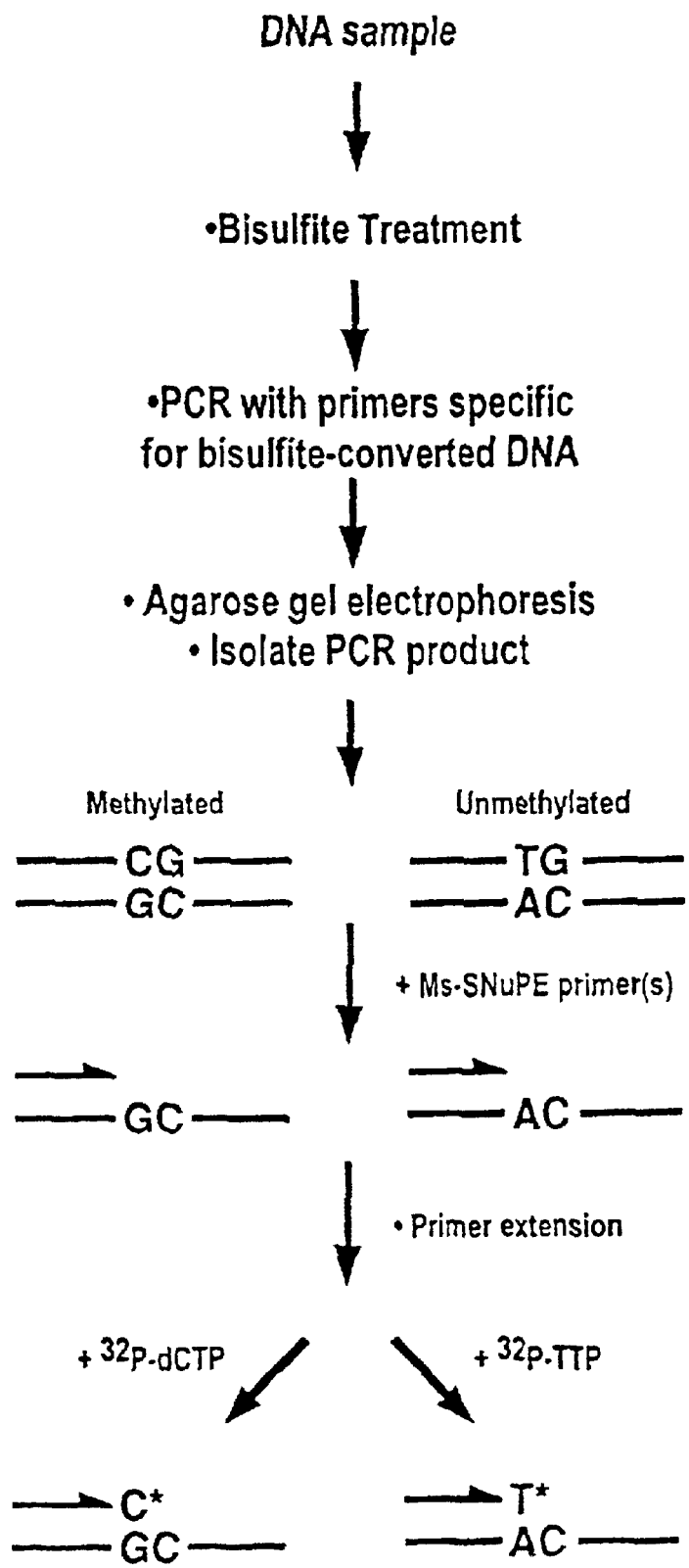
FIG. 1 shows a diagram of the inventive Ms-SNuPE assay for determination of strand-specific methylation status at cytosines. The process involves treating genomic DNA with sodium bisulfite, and generating a template by a PCR technique for a top strand methylation analysis. Alternatively a bottom strand methylation can also be assayed by designing the appropriate primers to generate a bottom strand-specific template. The process further entails amplifying the templates by a PCR technique. The PCR products are electrophoresed and isolated from agarose gels, followed by incubation with Ms-SNuPE primers, as disclosed herein wherein the Ms-SNuPE primers comprise a from about a 15 mer to about a 25 mer length primer that terminates immediately 5' of a single nucleotide to be assayed, and PCR buffer, [$^{32}$P]dNTPs and Taq polymerase for primer extension reactions. The radiolabeled products are separated, for example, by electrophoresis on polyacrylamide gels under denaturing conditions and visualized by exposure to autoradiographic film or phosphorimage quantitation.

The present invention provides a method for determining DNA methylation patterns at cytosine sites, comprising the steps of:

(a) obtaining genomic DNA from a DNA sample to be assayed, wherein sources of DNA include, for example, cell lines, blood, sputum, stool, urine, cerebrospinal fluid, paraffin-embedded tissues, histological slides and combinations thereof;

(b) reacting the genomic DNA with sodium bisulfite to convert unmethylated cytosine residues to uracil residues while leaving any 5-methylcytosine residues unchanged to provide primers specific for the bisulfite-converted genomic sample for top strand or bottom strand methylation analysis;

(c) performing a PCR amplification procedure using the top strand or bottom strand specific primers;

(d) isolating the PCR amplification products;

(e) performing a primer extension reaction using Ms-SNuPE primers, [$^{32}$P]dNTPs and Taq polymerase, wherein the Ms-SNuPE primers comprise a from about a 15 mer to about a 22 mer length primer that terminates immediately 5' of a single nucleotide to be assayed; and (f) determining the relative amount of allelic expression of CpG methylated sites by measuring the incorporation of different $^{32}$P-labeled dNTPs.

Preferably, the [$^{32}$P]NTP for top strand analysis is [$^{32}$P] dCTP or [32P]TTP. Preferably, the [$^{32}$P]NTP for bottom strand analysis is [$^{32}$P]dATP or [1$^{32}$P]dGTP. Preferably, the isolation step of the PCR products uses an electrophoresis technique. Most preferably, the electrophoresis technique uses an agarose gel.

DNA is isolated by standard techniques for isolating DNA from cellular, tissue or specimen samples. Such standard methods are found in textbook references such as Fritsch and Maniatis eds., *Molecular Cloning: A Laboratory Manual,* 1989.

The bisulfite reaction is performed according to standard techniques. For example and briefly, approximately 1 microgram of genomic DNA (amount of DNA can be less when using micro-dissected DNA specimens) is denatured for 15 minutes at 45° C. with 2N NaOH followed by incubation with 0.1 M hydroquinone and 3.6 M sodium bisulfite (pH 5.0) at 55° C. for 12 hours (appropriate range is 4–12 hours). The DNA is then purified from the reaction mixture using standard (commercially-available) DNA miniprep columns, or other standard techniques for DNA purification are also appropriate. The purified DNA sample is resuspended in 55 microliters of water and 5 microliters of 3N NaOH is added for a desulfonation reaction, preferably performed at 40° C. for 5–10 minutes. The DNA sample is then ethanol-precipitated and washed before being resuspended in an appropriate volume of water. Bisulfite treatment of DNA distinguishes methylated from unmethylated cytosines. The present bisulfite treatment method has advantages because it is quantitative, does not use restriction enzymes, and many CpG sites can be analyzed in each primer extension reaction by using a multiplex primer strategy.

The PCR amplification step (c) can be performed by standard PCR techniques, following a manufacturer's instructions. For example, approximately 1–2 microliters of the bisulfite-treated DNA was used as a template for strand-specific PCR amplification in a region of interest. In a PCR reaction profile for amplifying a portion of the p16 5' CpG island, for example, a procedure of initial denaturation of 94° C. for 3 minutes followed by a cycle of 94° C. of 30 seconds, 68° C. for 30 seconds, 72° C. for 30 seconds for a total of 30 cycles. The PCR reactions were performed in 25 microliter volumes under conditions of:~50 ng bisulfite-converted DNA (less for micro dissected samples), 10 mM Tris-HCl (pH 8.3), 1.5 mM $MgCl_2$, 50 mM KCl, 0.1% gelatin/ml, 100 $\mu$M of each of dNTP, 0.5 $\mu$M final concentration of each primer and 1 unit of Taq polymerase. There are many chromatographic techniques that can be used to isolate the PCR amplification products. In one illustrative procedure, approximately 10–25 microliters of the amplified PCR products were loaded onto 2% agarose gels and electrophoresed. The bands were visualized and isolated using standard get purification procedures.

The primer extension reaction is conducted using standard PCR primer extension techniques but using Ms-SNuPE primers as provided herein. Approximately 10–50 nanograms of purified PCR template is used in each Ms-SNuPE reaction. A typical reaction volume is about 25 microliters and comprises PCR template (about 10–50 ng), 1×PCR buffer, 1 $\mu$M of each Ms-SNuPE primer, 1 $\mu$Ci of the appropriate $^{32}$P-labeled dNTP (either [$^{32}$P]dCTP, [$^{32}$P]TTp, [$^{32}$P]dATP, [$^{32}$P]dGTP or combinations thereof), and 1 unit of Taq polymerase. As a general rule, oligonucleotides used in the primer extension reactions were designed to have annealing temperatures within 2–3° C. of each other and did not hybridize to sequences that originally contained CpG dinucleotides. The Ms-SNuPE reactions were performed at 95° C. for 1 minute, 50° C. for 2 minutes, and 72° C. for 1 minute. A stop solution (10 microliters) was added to the mixtures to terminate the reactions. The inventive Ms-SNuPE assay utilizes internal primer(s) which anneal to a PCR-generated template and terminate immediately 5' of the single nucleotide to be assayed. A similar procedure has been used successfully for detection of gene mutations Kuppuswamy et al., *Proc. Natl. Acad. Sci. USA* 88:1143–1147, 1991) and for quantitation of allele-specific expression (Szabo and Mann, *Genes Dev.* 9:3097–3108, 1995 and Greenwood and Burke, *Genome Res.* 6:336–348, 1996).

There are several techniques that are able to determine the relative amount of methylation at each CpG site, for example, using a denaturing polyacrylamide gel to measure $^{32}$P through phosphorimage analysis, or transfer of Ms-SNuPE reaction products to nylon membranes, or even using fluorescent probes instead of a $^{32}$P marker. In one method for determining the relative amount of methylation at each CpG site, approximately 1–2 microliters of each Ms-SNuPE reaction product was electrophoresed onto 15% denaturing polyacrylamide gel (7 M urea). The gels were transferred to filter paper and then dried. Phosphorimage analysis was performed to determine the relative amount of radiolabeled incorporation. An alternative method for determining the relative amount of methylation at individual CpG sites is by a direct transfer of the Ms-SNuPE reaction products to nylon membranes. This technique can be used to quantitate an average percent methylation of multiple CpG sites without using polyacrylamide gel electrophoresis. High-throughput methylation analysis was performed by direct transfer of the Ms-SNuPE reactions onto nylon membranes. A total of 100 microliters or 0.4 mM NaOH, 1 mM $Na_4P_2O_7$ was added to the completed primer extension reactions instead of adding stop solution. The mixture was directly transferred to nylon membranes using a dotblot vacuum manifold in a 96 well plate format. Each vacuum transfer well was washed a total of 4 times with 200 microliters of 2×SSC, 1 mM $Na_4P_2O_7$. The entire membrane was washed in 2×SSC, 1 mM $Na_4P_2O_7$. The radioactivity of each spot on the dried nylon membrane was quantitated by phosphorimaging analysis.

In the inventive quantitative Ms-SNuPE assay, the relative amount of allelic expression is quantitated by measuring the incorporation of different $^{32}$P-labeled dNTPs. FIG. 1 outlines how the assay can be utilized for quantitative methylation analysis. For example, the initial treatment of genomic DNA with sodium bisulfite causes unmethylated cytosine to be converted to uracil, which is subsequently replicated as thymine during PCR. Methylcytosine is resistant to deamination and is replicated as cytosine during amplification. Quantitation of the ratio of methylated versus unmethylated cytosine (C versus T) at the original CpG sites can be determined by incubating a gel-isolated PCR product, primer(s) and Taq polymerase with either [$^{32}$P]dCTP or [$^{32}$P]TTP, followed by denaturing polyacrylamide gel electrophoresis and phosphorimage analysis. In addition, opposite strand (bottom strand) Ms-SNuPE primers are further designed which would incorporate either [$^{32}$P]dATP or [$^{32}$P]dGTP to assess methylation status depending on which CpG site is analyzed.

Ms-SNuPE Primers

The present invention further provides a Ms-SNuPE primer sequence designed to anneal to and terminate immediately 5' of a desired cytosine codon in the CpG target site and that is located 5' upstream from a CpG island and are frequently hypermethylated in promoter regions of somatic genes in malignant tissue. Preferably, the Ms-SNuPE primer sequence comprises a sequence of at least fifteen bases having a sequence selected from the group consisting of GaL1 (SEQ ID NO:1), GaL2 (SEQ ID NO:2), GaL4 (SEQ ID NQ:3), HuN1 (SEQ ID NO:4), HuN2 (SEQ ID NO:5), HuN3 (SEQ ID NO:6), HuN4 (SEQ ID NO:7), HuN5 (SEQ ID NO:8), HuN6 (SEQ ID NO:9), CaS1 (SEQ ID NO:10), CaS2 (SEQ ID NO:11), CaS4 (SEQ ID NO:12), and combinations thereof. The present invention further provides a method for obtaining a Ms-SNuPE primer sequence, comprising finding a hypermethylated CpG island in a somatic gene om a malignant tissue or cell culture, determining the sequence located immediately 5' upstream from the hypermethylated CpG island, and isolating a 15 to 25 mer sequence 5' upstream from the hypermethylated CpG island for use as a Ms-SNuPE primer. The present invention further provides a Ms-SNuPE primer comprising a 15 to 25 mer oligonucleotide sequence obtained by the process comprising, (a) identifying hypermethylated CpG islands a somatic gene from a malignant tissue or cell culture source, (b) determining the sequence located immediately 5' upstream from the hypermethylated CpG island, and (c)

isolating at least a 15 mer sequence 5' upstream from the hypermethylated CpG island for use as a Ms-SNuPE primer. Preferably the Ms-SNuPE primer sequence is from about 15 to about 25 base pairs in length.

The ability to detect methylation changes associated with oncogenic transformation is of critical importance in understanding how DNA methylation may contribute to tumorigenesis. Regions of DNA that have tumor-specific methylation alterations can be accomplished using a variety of techniques. This will permit rapid methylation analysis of specific CpG sites using the inventive quantitative Ms-SNuPE primer process. For example, techniques such as restriction landmark genomic scanning (RLGS) (Hatada et al., *Proc. Natl. Acad. Sci. USA* 88:9523–9527, 1995), methylation-sensitive-representational difference analysis (MS-RDA) (Ushijima et al., *Proc. Natl. Acad. Sci. USA* 94:2284–2289, 1997) and methylation-sensitive arbitrarily primed PCR (AP-PCR) (Gonzalgo et al., *Cancer Res.* 57: 594–599, 1997) can be used for identifying and characterizing methylation differences between genomes.

Briefly, sequence determinations of regions of DNA that show tumor-specific methylation changes can be performed using standard techniques, such as those procedures described in textbook references such as Fritsch and Maniatis eds., *Molecular Cloning: A Laboratory Manual*, 1989. Additionally, commercially available kits or automated DNA sequencing systems can be utilized. Once specific regions of DNA have been identified by using such techniques, the Ms-SNuPE primers can be applied for rapidly screening the most important CpG sites that are involved with the specific methylation changes associated with a cancer phenotype.

EXAMPLE 1

This example illustrates a quantitative methylation analysis of three top strand sites in a 5' CpG island of p16 in various DNA samples using the inventive method. The top panel provides the locations of three sites analyzed (numbered 1, 2 and 3) relative to the putative transcriptional start sites (vertical arrows pointing upwards) and the exon 1α coding domain. The PCR primers used for top strand amplification of the 5' region of p16 (which includes putative transcriptional start sites) were 5'-GTA GGT GGG GAG GAG TTT AGT T-3' [SEQ ID NO. 13] and 5'-TCT AAT AAC CAACCA ACC CCT CC-3' [SEQ ID NO. 14]. The reactions were performed in 25 μl total volume under the conditions of 50 ng bisulfite-treated DNA, 10 mM Tris-HCl (pH 8.3), 1.5 mM MgCl$_2$, 50 mM KCl, 0.1% gelatin/ml, 100 μM of each dNTP, 0.5 μM final concentration of each primer and 1 U of Taq polymerase (Boehinger Mannheim, Indianapolis, Ind.). The reactions were hot-started using a 1:1 mixture of Taq/TaqStart antibody (Clontech, Palo Alto, Calif.).

An initial denaturation of 94° C. for 3 minutes was followed by 94° C. for 30 sec, 68° C. for 30 sec, 72° C. for 30 sec for a total of 35 cycles. The PCR products were separated by electrophoresis on 2% agarose gels and the bands were isolated using a Qiaquick™ gel extraction kit (Qiagen, Santa Clarita, Calif.).

The Ms-SNuPE reaction was performed in a 25 ml reaction volume with 10–50 ng of PCR template incubated in a final concentration of 1×PCR buffer, 1 μM of each Ms-SNuPE primer, 1 μCi of either [$^{32}$P]dCTP or [$^{32}$P]TTP and 1 U of Taq polymerase. The primer extensions were also hot-started using a 1: mixture of Taq/TaqStart antibody. The primers used for the Ms-SNuPE analysis were: site 1 5'-TTT TTT TGT TTG GAA AGA TAT-3' [SEQ ID NO. 15]; site 2 5'-TTT TAG GGG TGT TAT ATT-3' [SEQ ID NO. 16]; site 3 5'-TTT GAG GGA TAG GGT-3' [SEQ ID NO. 17]. The conditions for the primer extension reactions were 95° C. for 1 minute, 50° C. for 2 minutes and 70° C. for 1 minute. A stop solution (10 μl) was added to the reaction mixtures and the samples were loaded onto 15% denaturing polyacrylamide gels (7 M urea). Radioactivity of the bands was quantitated by phosphorimaging analysis. The control sets included "M" PCR product amplified from a plasmid containing bisulfide-specific methylated sequence; "U" PCR product amplified from a plasmid containing bisulfite-specific unmethylated sequence; and "mix" a 50:50 mixture of methylated and unmethylated PCR-amplified plasmid sequences. The DNA samples analyzed included T24 and J82 bladder cancer cell lines; wbc (white blood cell), melanoma (primary melanoma tumor tissue sample), and bladder (primary bladder tumor tissue sample). The tissue samples were micro dissected from paraffin-embedded tumor material. The grid at the bottom of the lower panel shows the ratio of methylated (C) versus unmethylated (T) bands at each site based upon phosphorimage quantitation.

Figure 2:
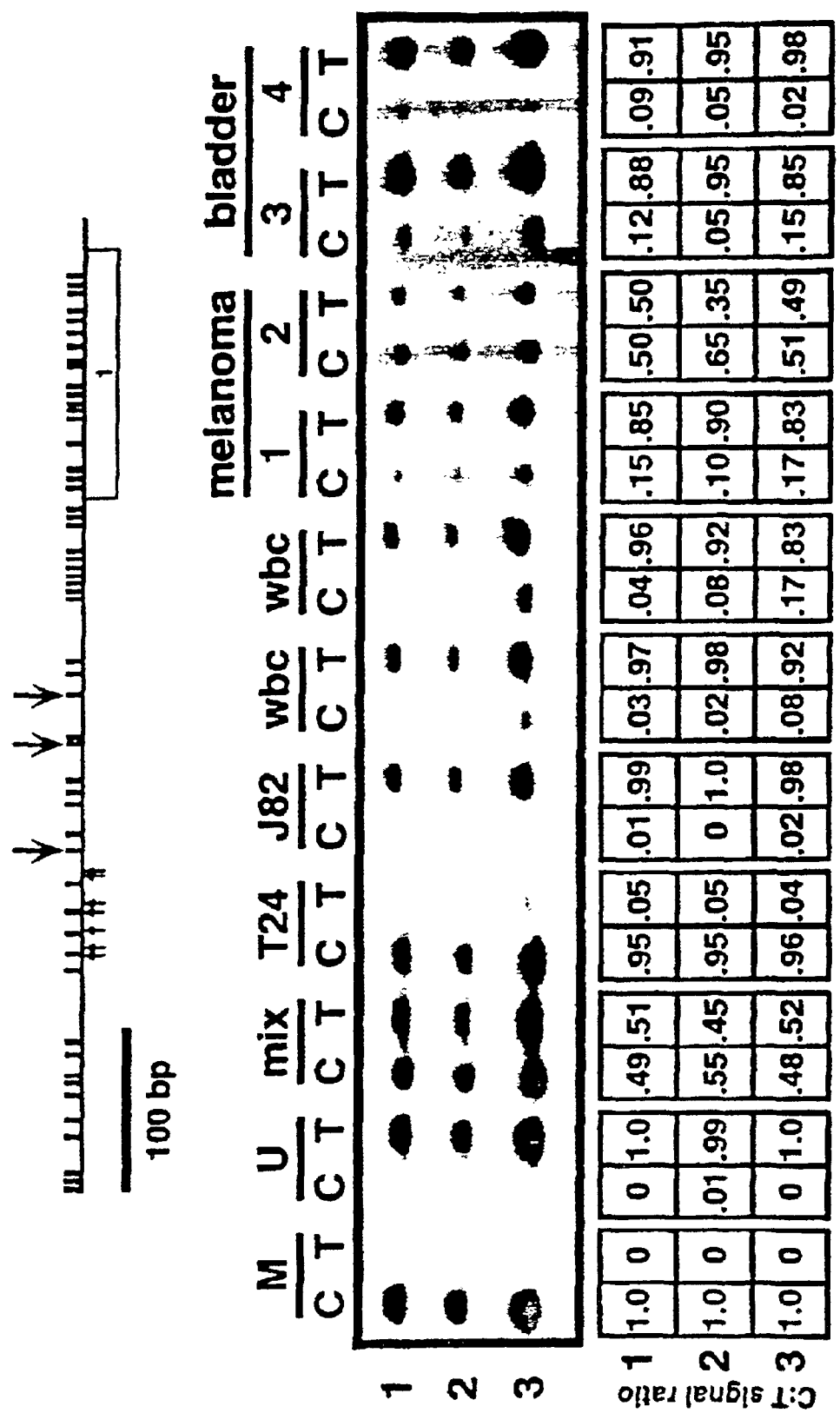
FIG. 2 shows the results from a quantitative methylation analysis of three top strand CpG sites from a 5' CpG island of p16. P16 is a known tumor suppressor gene and the particular region examined for changes in methylation is the promoter region of this gene. The top panel provides the locations of three sites analyzed (numbered 1, 2 and 3) relative to the putative transcriptional start sites (vertical arrows pointing upwards) and the exon 1α coding domain. The PCR primers used for top strand amplification of the 5' region of p16 (which includes putative transcriptional start sites) were 5'-GTA GGT GGG GAG GAG TTT AGT T-3' [SEQ ID NO. 13] and 5'-TCT AAT AAC CAA CCA ACC CCT CC-3' [SEQ ID NO. 14]. The control sets included "M" PCR product amplified from a plasmid containing bisulfide-specific methylated sequence; "U" PCR product amplified from a plasmid containing bisulfite-specific unmethylated sequence; and "mix" a 50:50 mixture of methylated and unmethylated PCR-amplified plasmid sequences. The DNA samples analyzed included T24 and J82 bladder cancer cell lines; wbc (white blood cell), melanoma (primary melanoma tumor tissue sample), and bladder (primary bladder tumor tissue sample). The tissue samples were micro dissected from paraffin-embedded tumor material. The grid at the bottom of the lower panel shows the ratio of methylated (C) versus unmethylated (T) bands at each site based upon phosphorimage quantitation.

These data (FIG. 2) show the ability of the inventive assay to detect altered patterns of methylation.

EXAMPLE 2

Figure 3:
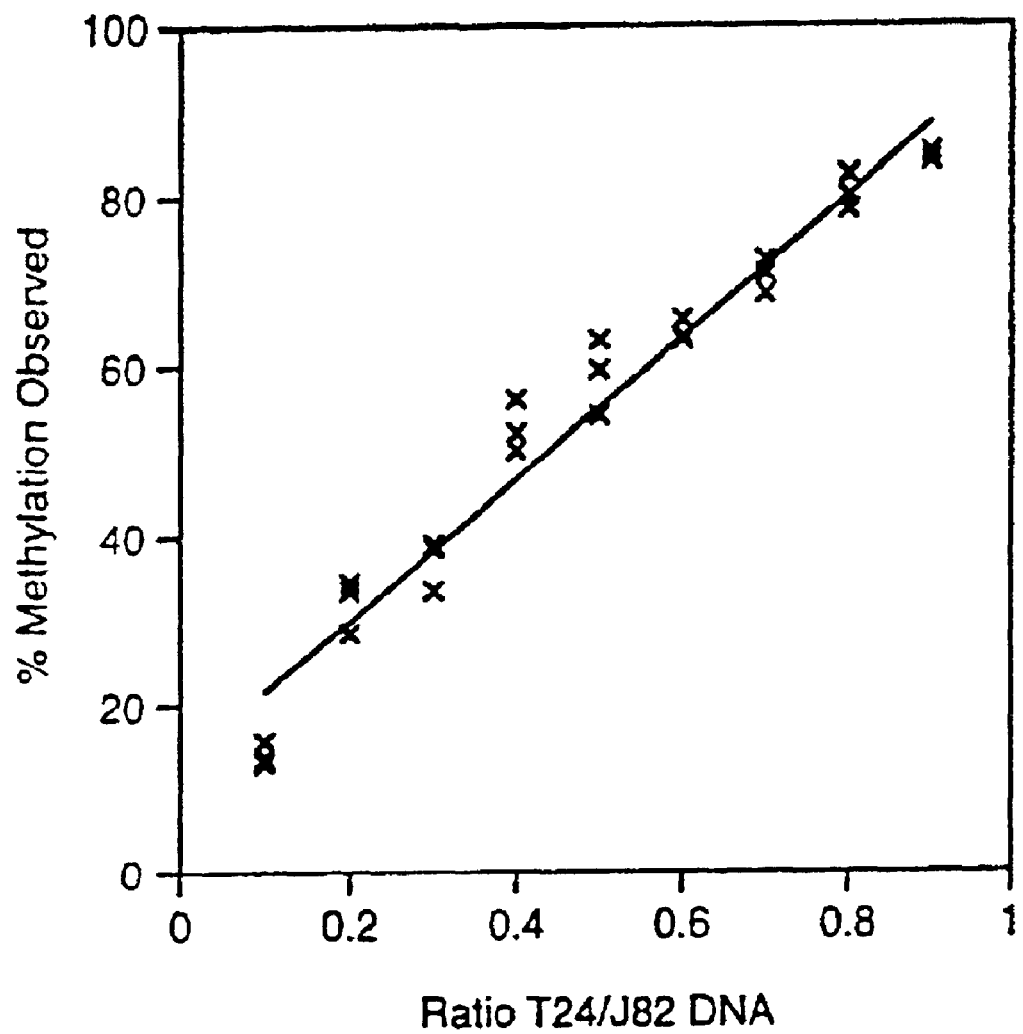
FIG. 3 shows a mixing experiment showing a linear response of the inventive Ms-SNuPE assay for detection of cytosine methylation. A T24 bladder cancer cell line DNA (predominantly methylated) was added in increasing amounts to a J82 bladder cancer cell line DNA (predominantly unmethylated).
Figure 4:
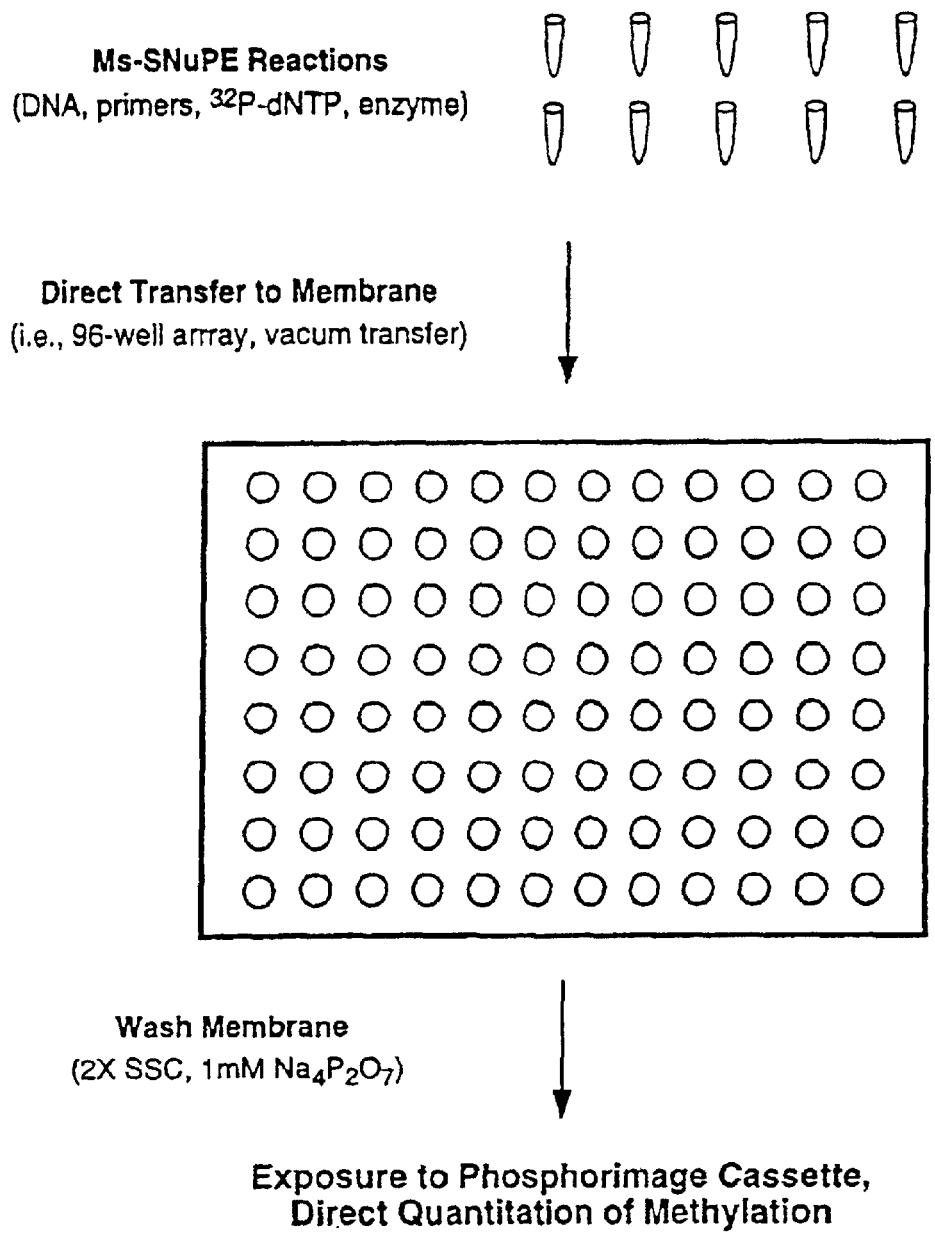
FIG. 4 shows a schematic diagram that outlines a process for a high-throughput methylation analysis. The Ms-SNuPE primer extension reactions are performed and then the products are directly transferred to membranes, preferably nylon membranes. This allows for a large number of samples to be analyzed simultaneously in a high-density format. The membrane is washed and exposed to a phosphorimage cassette for quantitative methylation analysis and eliminate the need for polyacrylamide gel electrophoresis for data measurement.
Figure 5:
FIG. 5 (Panel A) shows results from quantitative analysis of DNA methylation using the Ms-SNuPE blot transfer technique of FIG. 4. Levels of DNA methylation in matched normal and tumor colon specimens were analyzed in the 5' promoter region of the p16 gene. The average methylation of 3 sites in the p16 promoter (FIG. 2) was determined by quantitating the C:T signal ration by phosphorimage analysis. Panel B shows the results of quantitating the average methylation of 3 CpG sites using standard polyacrylamide gel electrophoresis compared to dot blot transfers. The average methylation of the monitored sites in various colon specimens is plotted on the graph and shows little difference between quantitated values derived from polyacrylamide gel electrophoresis compared tom the dotblot technique. These data show the feasibility of using the Ms-SNuPE dotblot procedure for high-throughput detection and quantitation of DNA methylation changes in cancer cells.
Figure 5:
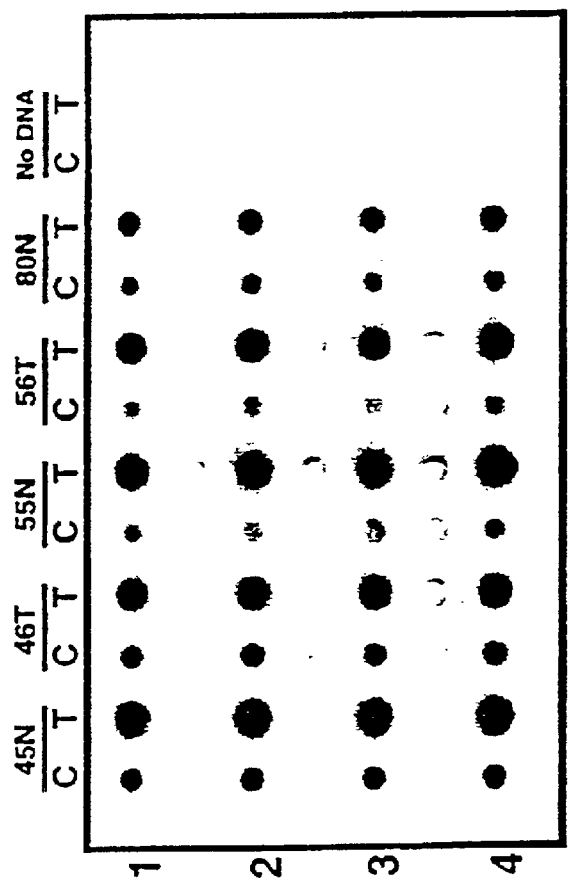
Figure 5:
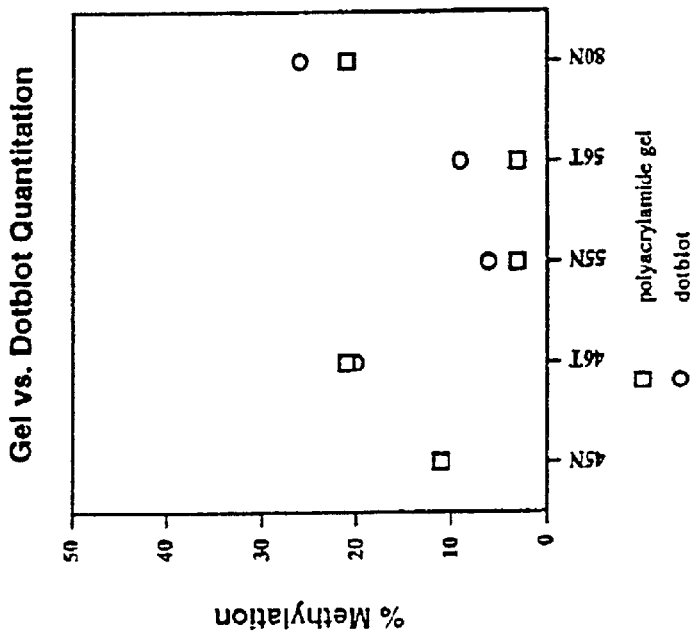

This example illustrates a mixing experiment showing a linear response of the inventive Ms-SNuPE assay for detection of cytosine methylation. A T24 bladder cancer cell line DNA (predominantly methylated) was added in increasing amounts to a J82 bladder cancer cell line DNA (predominantly unmethylated). FIG. 3 shows data from an 18 mer oligonucleotide [SEQ ID NO. 16] which was used in multiplex analysis of CpG methylation (site 2) of the p16 5' CpG in combination with a 15-mer and 21-mer primer [SEQ ID NOS 17 and 15, respectively] (correlation coefficient= 0.99). Both the 15 mer and 21-mer produced a nearly identical linear response as the 18-mer. FIG. 3 shows data from three separate experiments. Differential specific activity and incorporation efficiency of each [$^{32}$P]dNTP was controlled for by using a 50:50 mixture of bisulfite-specific methylated versus unmethylated PCR template for analysis.

EXAMPLE 3

This example provides a summary of DNA regions for which Ms-SNuPE primers can be designed and the inventive method applied for a quantitative detection of abnormal DNA methylation in cancer cells. The sequences are listed according to name, size and frequency of hypermethylation in the corresponding cell line or primary tumor.

| fragment | size (bp) | methylated in colon cell line | hypermethylated in colon cancer | hypermethylated in bladder cancer | comments |
| --- | --- | --- | --- | --- | --- |
| GaL1 | 530 | 7/7 (100%) | 3/7 (42%) | 3/7 (42%) | GC content (0.6), observed/expected CpG (0.63) |

-continued

| fragment | size (bp) | methylated in colon cell line | hypermethylated in colon cancer | hypermethylated in bladder cancer | comments |
|---|---|---|---|---|---|
| GaL2 | 308 | 7/7 (100%) | 4/5 (80%) | 6/7 (85%) | GC content (0.6), observed/expected CpG (0.6) |
| GaL4 | 177 | 7/7 (100%) | 1/2 (50%) | 3/4 (75%) | GC content (0.59), observed/expected CpG (0.50) |
| CaS1 | 215 | 4/7 (57%) | 0/5 (0%) | 2/7 (28%) | GC content (0.55), observed/expected CpG (0.78) |
| CaS2 | 220 | 4/7 (57%) | 3/5 (60%) | 3/7 (42%) | GC content (0.54), observed/expected CpG (0.74) |
| CaS4 | 196 | 6/7 (85%) | 0/5 (0%) | 1/7 (14%) | GC content (0.64), observed/expected CpG (0.84) |
| HuN1 | 148 | 7/7 (100%) | 3/5 (60%) | 3/7 (42%) | GC content (0.54), observed/expected CpG (0.99) |
| HuN2 | 384 | 7/7 (100%) | 4/5 (80%) | 2/7 (28%) | GC content (0.6), observed/expected CpG (0.62) |
| HuN3 | 178 | 6/7 (85%) | 4/5 (80%) | 3/7 (42%) | GC content (0.53), observed/expected CpG (0.97) |
| HuN4 | 359 | 7/7 (100%) | 3/5 (60%) | 4/7 (57%) | GC content (0.51), observed/expected CpG (0.47) |
| HuN5 | 251 | 7/7 (100%) | 2/5 (40%) | 5/7 (71%) | GC content (0.63), observed/expected CpG (0.77) |
| HuN6 | 145 | 6/7 (85%) | 3/4 (75%) | 1/2 (50%) | GC content (0.55), observed/expected CpG (0.47) |

We claim:

1. A diagnostic method for colon or bladder cancer, comprising:
   (a) obtaining an isolated test genomic DNA sample from a test tissue;
   (b) subjecting the test genomic DNA sample to methylation analysis, whereby the methylation state of one or more CpG dinucleotide sequences within a sequence selected from the group consisting of SEQ ID NOS:1–9 and 11, and fragments thereof comprisin at least 16 contiguous bases is determined; and
   (c) comparing the methylation state of the one or more CpG dinucleotide sequences of the test sample with that of corresponding sequences of a reference genomic sample from a reference genomic tissue, or with that of a corresponding known reference methylation state, thereby providing, at least in part, a colon or bladder cancer diagnosis.

2. The diagnostic method of claim 1, wherein the test tissue is cancer tissue or putative cancer tissue, and wherein the reference tissue or reference methylation state is that of corresponding normal tissue, or corresponds to a known methylation state of corresponding normal tissue, respectively.

3. The diagnostic method of claim 1, wherein the methylation analysis comprises a method selected from the group consisting of DNA sequencing using bisulfite treatment, restriction landmark genomic scanning, methylation-sensistie arbitrarily primed PCR, Southern analysis using a methylation-sensitive restriction enzyme, methylation-specific PCR, restriction enzyme digestion of PCR products amplified from bisulfite-converted DNA, and combinations thereof.

4. The diagnostic method of claim 1, where the methylation analysis comprises:
   (a) reacting the test genomic DNA sample with sodium bisulfite to convert unmethylated cytosine residues to uracil residues while leaving any 5-methylcytosine residues unchanged to create an exposed bisulfite-converted DNA sample having binding sites for primers specific for the bisulfite-converted DNA sample;
   (b) performing a PCR amplification procedure using top strand or bottom strand specific primers;
   (c) isolating the PCR amplification products;
   (d) performing a primer extension reaction using a Ms-SNuPE primer, dNTPs and Taq polymerase, wherein the Ms-SNuPE primer comprises from about a 15-mer to about a 22-mer length primer sequence that is complementary to the bisulfite-converte DNA sample and terminates immediately 5' of the cytosine residue of the one or more CpG dinucleotide sequences to be assayed; and
   (f) determining the methylation state of the one or more CpG dinucleotide sequences by determining the identity of the first primer-extended base.

5. The diagnostic method of claim 4, wherein the dNTPs are labeled with a label selected from the group consisting of radiolabels and fluorescent labels, and wherein determining the identity of the first primer-extended base is by measuring incorporation of the labeled dNTPs.

6. A diagnostic method for bladder cancer, comprising:
   (a) obtaining an isolated test genomic DNA sample from a test tissue;
   (b) subjecting the test genomic DNA sample to methylation analysis, whereby the methylation state of one or more CpG dinucleotide sequences within a sequence selected from the group consisting of SEQ ID NOS:1–9 and 11, and fragments thereof comprising at least 16 contiguous bases is determined; and
   (c) comparing the methylation state of the one or more CpG dinucleotide sequences of the test sample with that of corresponding sequences of a reference genomic sample from a reference genomic tissue, or with that of a corresponding known reference methylation state, thereby providing, at least in part, a bladder cancer diagnosis.

7. The diagnostic method of claim 6, wherein the test tissue is cancer tissue or putative cancer tissue, and wherein the reference tissue or reference methylation state is that of corresponding normal tissue, or corresponds to a known methylation state of corresponding normal tissue, respectively.

8. The diagnostic method of claim 6, wherein the methylation analysis comprises a method selected from the group consisting of DNA sequencing using bisulfite treatment, restriction landmark genomic scanning, methylation-sensitive arbitrarily primed PCR, Southern analysis using a methylation-sensitive restriction enzyme, methylation-specific PCR, restriction enzyme digestion of PCR products amplified from bisulfite-converted DNA, and combinations thereof.

9. The diagnostic method of claim 6, wherein the methylation analysis comprises:
   (a) reacting the test genomic DNA sample with sodium bisulfite to convert unmethylated cytosine residues to uracil residues while leaving any 5-methylcytosine residues unchanged to create an exposed bisulfite-converted DNA sample having binding sites for primers specific for the bisulfite-converted DNA sample;

(b) performing a PCR amplification procedure using top strand or bottom strand specific primers;

(c) isolating the PCR amplification products;

(d) performing a primer extension reaction using a Ms-SNuPE primer, dNTPs and Taq polymerase, wherein the Ms-SNuPE primer comprises from about a 15-mer to about a 22-mer length primer sequence that is complementary to the bisulfite-converte DNA sample and terminates immediately 5' of the cytosine residue of the one or more CpG dinucleotide sequences to be assayed; and (f) determining the methylation state of the one or more CpG dinucleotide sequences by determining the identity of the first primer-extended base.

10. The diagnostic method of claim 9, where the dNTPs are labeled with a label selected from the group consisting of radiolabels and fluorescent labels, and wherein determining the identity of the first primer-extended base is by measuring incorporation of the labeled dNTPs.

* * * * *

UNITED STATES PATENT AND TRADEMARK OFFICE
CERTIFICATE OF CORRECTION

| | |
|---|---|
| PATENT NO. | : 6,811,982 B2 |
| APPLICATION NO. | : 10/109725 |
| DATED | : November 2, 2004 |
| INVENTOR(S) | : Mark L. Gonzalgo, Peter A. Jones and Gangning Liang |

Page 1 of 1

It is certified that error appears in the above-identified patent and that said Letters Patent is hereby corrected as shown below:

Column 1, line 19 (prior to "Background of the Invention"), the following paragraph text should be added:

--FEDERAL FUNDING ACKNOWLEDGEMENT

This invention was made with government support under Contract No. R35 CA049758 awarded by the National Institutes of Health. The government has certain rights in the invention.--

Column 19, line 28, the word "comprisin" should read "comprising", and at Column 19, lines 46-47, the words "methylation-sensistie" should read "methylation-senstitive".

Column 20, line 19, the words "bisulfite-converte" should read "bisulfite-converted", and at Column 20, line 23, the word "(f)" should read "(e)".

Signed and Sealed this

Ninth Day of February, 2010

David J. Kappos
*Director of the United States Patent and Trademark Office*